United States Patent [19]

Pirkl

[11] Patent Number: 4,754,146
[45] Date of Patent: Jun. 28, 1988

[54] SUN-TANNING APPARATUS
[75] Inventor: Josef Pirkl, Ratingen, Fed. Rep. of Germany
[73] Assignee: Quarzlampenfabrik-Dr. Ing. Felix W. Muller GmbH & Co. KG, Essen, Fed. Rep. of Germany
[21] Appl. No.: 902,406
[22] PCT Filed: Dec. 4, 1985
[86] PCT No.: PCT/EP85/00669
§ 371 Date: Aug. 12, 1986
§ 102(e) Date: Aug. 12, 1986
[87] PCT Pub. No.: WO86/03682
PCT Pub. Date: Jul. 3, 1986

[30] Foreign Application Priority Data
Dec. 19, 1984 [DE] Fed. Rep. of Germany ... 8437162[U]
Oct. 3, 1985 [DE] Fed. Rep. of Germany ... 8528202[U]

[51] Int. Cl.⁴ ............................................. G21G 4/00
[52] U.S. Cl. ............................. 250/494.1; 250/493.1
[58] Field of Search ............. 250/493.1, 494.1, 504 R; 128/373, 376

[56] References Cited
U.S. PATENT DOCUMENTS
4,335,724 6/1982 Frei et al. ......................... 250/494.1

FOREIGN PATENT DOCUMENTS
2601935 7/1977 Fed. Rep. of Germany .
3225544 1/1984 Fed. Rep. of Germany .
3331051 3/1985 Fed. Rep. of Germany .
2539555 7/1984 France .
2149490 6/1985 United Kingdom .

Primary Examiner—Bruce C. Anderson
Attorney, Agent, or Firm—Karl F. Ross; Herbert Dubno

[57] ABSTRACT

A sun-tanning apparatus has a supporting or bed surface and a plurality of low-pressure UV-A tubes arranged parallel to and at a distance from each other as radiation generators in a housing of the apparatus, the UV-A tubes being installed in a trough-like reflector and being covered on top by the supporting surface that rests on the side walls of the housing and which permits the passage of UA-V radiation. A largely even and flat radiation outlet is provided immediately above the supporting surface by using spacers arranged over the length and/or breadth of the apparatus between the low-pressure UA-V tubes, the supporting surface resting on the upper ends of said spacers, the lower ends of said spacers being attached in or on the base of the reflector. The spacers are a plurality of stand-off bolts that are distributed over the length and breadth of the apparatus, the supporting surface resting on the upper ends of the bolts, the lower ends of the bolts being secured in the base of the reflector. As well, it is also possible that the spacers consist of spacer profiles that extend wholly or in part over the length of the apparatus, the supporting surface resting on the upper ends of these spacer profiles, the lower ends being secured to the base of the reflector.

9 Claims, 3 Drawing Sheets

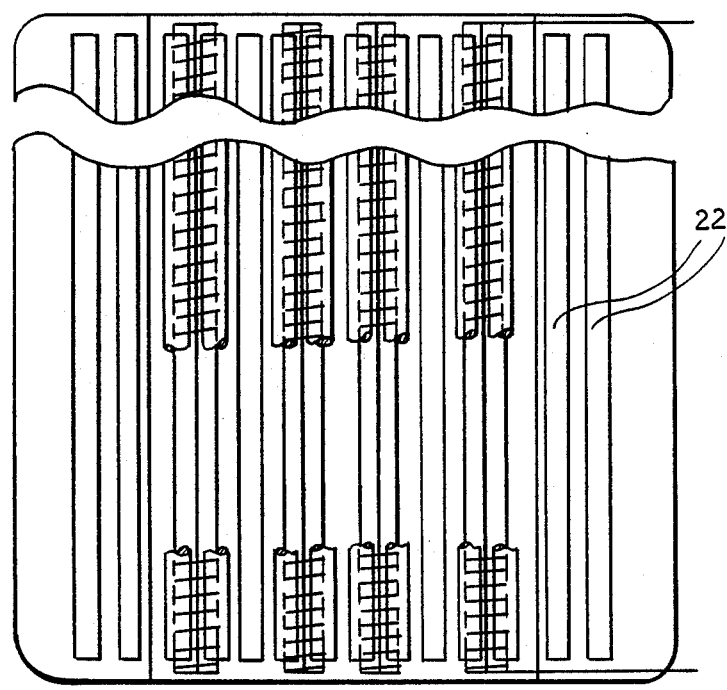
FIG.5
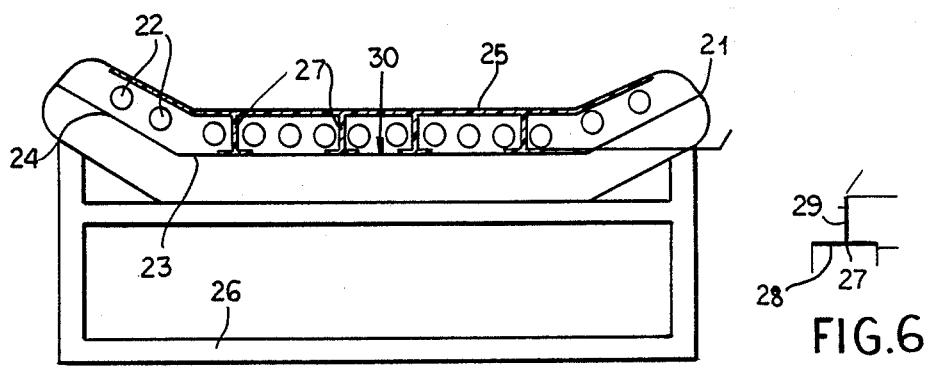
FIG.4
FIG.6

SUN-TANNING APPARATUS

CROSS REFERENCE TO RELATED APPLICATIONS

The present application is a national phase application corresponding to PCT/EP 85/00669 filed Dec. 4, 1985 and based, in turn, on German Utility Models G 84 37 162.5 of Dec. 19, 1984 and G 85 28 202.2 of Oct. 3, 1985 under the International Convention.

FIELD OF THE INVENTION

The present invention relates to a sun-tanning apparatus comprising a bed-type supporting surface and a plurality of low-pressure A-type ultraviolet (UV-A) tubes arranged within a housing of the apparatus that are used as radiation generators, said tubes being arranged parallel to and at a distance from each other. These tubes are arranged in a trough-like reflector and are covered above by a supporting or bed surface that rests on the side walls of the housing and which is transparent to A-type ultraviolet radiation.

BACKGROUND OF THE INVENTION

Sun-tanning devices of this kind are known. Usually, these devices contain 10 to 20 low-pressure UV-A types, each of which is surrounded by a trough-shaped reflector, with an angle of at least 180° between the axes. These reflectors are supported in the housing of the sun-tanning apparatus. The supporting or bed surface is supported on the side walls of the housing and also on the face edges of the individual reflectors that project above the low-pressure tubes. These known devices have the disadvantage that because the supporting surface lies on the face edges of the reflectors, a striped pattern results from the UV-A radiation that emerges, as almost no radiation emerges in the area of the face edges of the reflectors but only in the area of the reflector openings.

SUMMARY OF THE INVENTION

The present invention is directed to an improved sun-tanning apparatus of the type described above, wherein a largely even, flat radiation outlet area is provided. Thus there is provided a sun-tanning apparatus comprising a supporting surface, and a plurality of low-pressure UV-A tubes arranged within a housing of the apparatus parallel to and at a distance from each other, said tubes being located in a trough-like reflector and covered on top by a supporting surface that rests on the side walls of the housing and which permits the passage of UV-A radiation, wherein between the low-pressure UV-A tubes there are spacers distributed over the entire length and/or breadth of the apparatus in between the low pressure UV-A tubes, the supporting surface resting on the upper end of these spacers, the lower end of said spacers being secured in or on the base of the reflector.

According to the present invention, spacers are arranged between the low-pressure UV-A tubes, the spacers being distributed over the length and/or breadth of the apparatus, wherein the supporting surface rests on the upper end of the spacers and the lower end of the spacers is secured in or on the base of the reflector. Thus the supporting surface is supported only in the region of the spacers so that the radiation emitted from the low-pressure UV-A tubes can pass almost completely unhindered to the outside through the supporting surface.

In one embodiment the spacers are a plurality of stand-off bolts that are distributed over the length and breadth of the apparatus, the supporting surface resting on the upper end of the bolts, the lower end of the bolts being secured in the base of the reflector.

The stand-off bolts are arranged in rows in the longitudinal and/or transverse direction of the apparatus. In a preferred embodiment there are four rows of stand-off bolts, located between the second, fifth, eighth and eleventh low-pressure UV-A tubes, with a total of thirteen tubes being provided.

It is preferred that the stand-off bolts be in a symmetrical arrangement in order to achieve completely even support for the bed or supporting surface.

However, it is also possible to use an asymmetrical arrangement, such that the stand-off bolts that make up the individual rows are staggered or are placed at irregular intervals.

The stand-off bolts are in the form of studs, the lower end of which are screwed into nuts that are attached to the underside of the reflector base. A nut is provided on the inner side of the reflector and acts as a lock nut and serves to allow for precise adjustment of the stand-off distance, such that the supporting surface lies evenly on the face sides of the stand-off bolts.

In a second embodiment the spacers are spacer profiles that extend wholly or in part over the length of the apparatus, the supporting surface resting on one face end of said profiles and the other end faces of the profiles being secured to the base of the reflector.

It is preferred that the spacers be configured as T-spacers. The horizontal arms of the T-spacers are secured to the base of the reflector, for example by being screwed into position, by rivetting, cementing, or the like, whereas the supporting surface is installed on the face sides of the vertical arms of the T-spacers.

It is advantageous that there by four spacer sections in the horizontal portion of the reflector, each of which has two or three low-pressure UV-A tubes.

According to another feature of the present invention the spacer profiles are produced from material that permits the passage of UV-A radiation, so that the radiation emitted from adjacent low-pressure UV-A tubes can pass to the outside relatively unhindered. To this end it is preferred that the spacer profile be of acrylic glass.

The spacer profiles are 2-4 mm thick, which is adequate to withstand the loads to which the supporting surface is subjected.

It is advantageous to use low-pressure UV-A tubes that have their lower halves, as viewed in cross-section, internally silvered so that the radiation is reflected within the tubes and radiated to the outside through the supporting surface. Radiation that emerges and strikes the reflector will be reflected in the conventional manner.

BRIEF DESCRIPTION OF THE DRAWING

By way of illustration but not limitation, embodiments of the present invention are hereinafter described with reference to the drawing, in which:

FIG. 4 is a sectioned front view of a second embodiment of a sun-tanning apparatus;

FIG. 5 is a plan view of FIG. 4, without a supporting surface; and

FIG. 6 is a view of the spacer profiles as in FIG. 4 and FIG. 5.

DESCRIPTION

Figure 1:
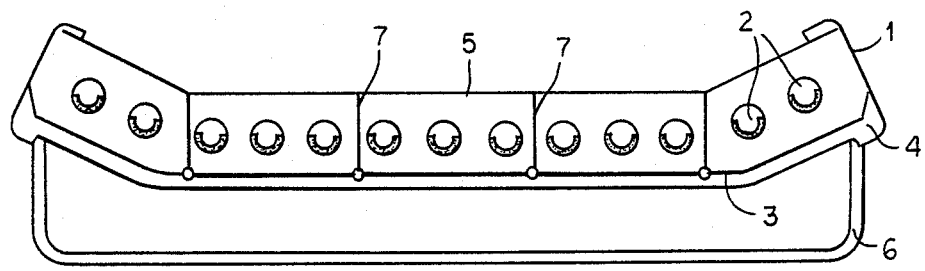
FIG. 1 is a cross sectional view of an embodiment of a sun-tanning apparatus.
Figure 2:
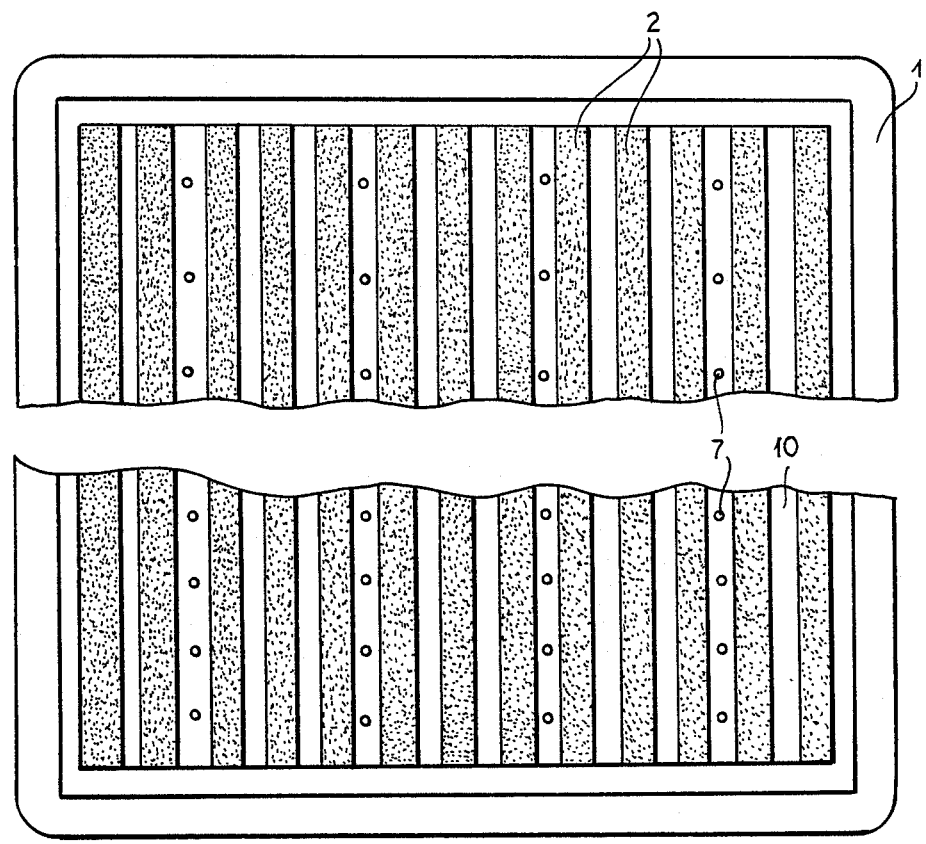
FIG. 2 is a plan view of FIG. 1, without a supporting surface.
Figure 3:
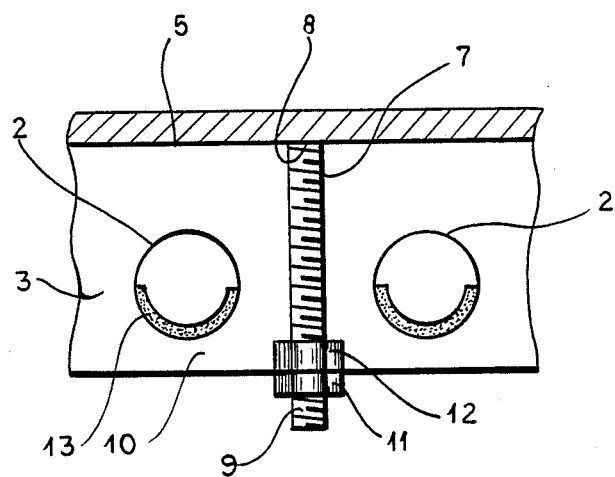
FIG. 3 is a sectional view of a region of the sun-tanning apparatus of FIG. 1.

In the embodiment shown in FIGS. 1 to 3, a housing 1 of the sun-tanning apparatus contains a plurality of low pressure UV-A tubes 2 that constitute a source of radiation. These tubes are arranged parallel to and at a distance from each other. in the illustrated embodiment, thirteen such low-pressure UV-A tubes 2 are used. The low-pressure UV-A tubes 2 are arranged in a trough-like reflector 3, the long sides 4 of which are angled upwards at either end. The low-pressure UV-A tubes 2 are covered by a supporting surface 5, the edges of which rest on the side walls of the housing 1. The housing 1 is supported at both ends on feet 6 that are of an approximate U-shaped cross-section.

A plurality of stand-off bolts 7 are installed over the length and breadth of the apparatus between the low-pressure UV-A tubes, the supporting surface 5 resting on the upper end of these stand-off bolts and the lower end of the bolts 9 being secured in the base 10 of the reflector 3.

The stand-off bolts 7 are arranged in rows in the longitudinal and the transverse directions of the apparatus. In the embodiment shown, there are a total of four rows of stand-off bolts 7, with one row of the stand-off bolts 7 being located behind the second, fifth, eighth, and eleventh low-pressure UV-A tubes 2. In the embodiment shown, the arrangement of the stand-off bolts 7 is symmetrical.

The stand-off bolts 7 are secured by threaded nuts 11 that are welded to the base of the reflector 3, the stand-off bolts in the form of studs being screwed into these threaded nuts. Lock-nuts 12 are provided inside the reflector 3 and these are screwed onto the stand-off bolts 7. Using these lock-nuts 12 it is possible to adjust the height of the stand-off bolts very precisely, such that the supporting surface 5 lies evenly on one end 8 of the stand-off bolts 7.

The low-pressure UV-A tubes that are used have the lower halves 13 of their cross-sections mirrored or silvered on the inside. By installing such internally mirrored low-pressure UV-A tubes one can use a trough-like reflector 3 so that the previously used individual reflectors can be dispensed with.

In the embodiment shown in FIGS. 4 to 6 the housing is represented at 21. Within this housing there are a plurality of low-pressure UV-A tubes 22 that are arranged parallel to and at a distance from each other. The low-pressure UV-A tubes 22 are arranged in a trough-like reflector 23, the long sides 24 of which are angled upwards at either side. The low-pressure UV-A tubes 22 are covered by a supporting surface 25, the edges of which rest on the side walls of the housing 21. An acrylic glass panel serves as the supporting surface 25. The housing itself is supported at both ends by feet 26 that are of approximate U-shaped cross-section.

Spacer profiles 27 extend over the whole length of the apparatus 21 in between the low-pressure UV-A tubes. These spacer profiles are of T-section. The horizontal arms 28 of the T-profiles are secured to the base of the reflector 23, for example, by screws, rivets, cement, or the like, while the supporting surface 25 rests on the face ends of the vertical columns 29.

In the embodiment shown, ten low pressure UV-A tubes 22 are arranged in the horizontal portion of the reflector, there being four spacer profiles 27 between which there are in each instance two or three low-pressure UV-A tubes 22.

Since the spacer profiles are produced from material that permits the passage of UV-A radiation, the radiation can pass practically unhindered through the supporting surface 25 to the outside.

The present invention results in a particularly simple solution to supporting the surface 25, which also ensures the largely unhindered passage of the radiation.

The embodiments of the invention in which an exclusive property or privilege is claimed are defined as follows:

1. A sun-tanning apparatus, comprising:
   a trough-shaped upwardly concave reflector;
   a plurality of mutually parallel transversely spaced ultraviolet-radiating tubes mounted in said reflector;
   a supporting surface transmissive to ultraviolet radiation for a person to be tanned by ultraviolet radiation from said tubes spanning said reflector above said tubes; and
   rows of spaced-apart spacers between said tubes, braced upon said reflector and engaging said surface from below to support said surface upon said reflector at a multiplicity of discrete points spaced apart over the length and breadth of said surface.

2. The sun-tanning apparatus defined in claim 1 wherein said spacers are stand-off bolts having upper ends upon which said surface rests and lower ends secured to said reflector.

3. The sun-tanning apparatus defined in claim 2 wherein said stand-off bolts are arrayed in rows extending both longitudinally and tranversely of the apparatus.

4. The sun-tanning apparatus defined in claim 2 wherein four rows of said stand-off bolts are provided.

5. The sun-tanning apparatus defined in claim 20 wherein the stand-off bolts are staggered from row to row.

6. The sun-tanning apparatus defined in claim 2 wherein a respective attachment nut is secured to said reflector to receive each of said stand-off bolts and said stand-off bolts are threadedly engaged in the respective nuts.

7. The sun-tanning apparatus defined in claim defined in claim 6, further comprising a locknut threaded onto each stand-off bolt for locking same in the respective attachment nut.

8. A sun-tanning apparatus, comprising:
   a trough-shaped upwardly concave reflector;
   a plurality of mutually parallel transversely spaced ultraviolet-radiating tubes mounted in said reflector;
   a supporting surface transmissive to ultraviolet radiation for a person to be tanned by ultraviolet radiation from said tubes spanning said reflector above said tubes; and
   a plurality of spacers between said tubes, braced upon said reflector and engaging said surface from below to support said surface upon said reflector at a plurality of locations.

9. A sun-tanning apparatus, comprising:

a trough-shaped upwardly concave reflector;

a plurality of mutually parallel transversely spaced ultraviolet-radiating tubes mounted in said reflector;

a supporting surface transmissive to ultraviolet radiation for a person to be tanned by ultraviolet radiation from said tubes spanning said reflector above said tubes;

rows of spaced-apart spacers between said tubes, braced upon said reflector and engaging said surface from below to support said surface upon said reflector at a multiplicity of discrete points spaced apart over the length and breadth of said surface; and adjusting means for each of said spacers selectively varying the distance from said reflector at which each of said spacers engages said surface from below.

* * * * *